United States Patent
Noguchi et al.

(10) Patent No.: US 8,413,516 B2
(45) Date of Patent: Apr. 9, 2013

(54) ELASTIC WAVE MEASUREMENT APPARATUS AND METHOD

(75) Inventors: Kazuhiro Noguchi, Tokyo (JP); Noritaka Nakaso, Tokyo (JP)

(73) Assignee: Toppan Printing Co., Ltd., Tokyo (JP)

( * ) Notice: Subject to any disclaimer, the term of this patent is extended or adjusted under 35 U.S.C. 154(b) by 260 days.

(21) Appl. No.: 12/659,701

(22) Filed: Mar. 17, 2010

(65) Prior Publication Data
US 2010/0170345 A1    Jul. 8, 2010

Related U.S. Application Data

(63) Continuation of application No. PCT/JP2008/065902, filed on Sep. 3, 2008.

(30) Foreign Application Priority Data

Sep. 19, 2007   (JP) .................................. 2007-243073

(51) Int. Cl.
*G01N 29/22* (2006.01)
(52) U.S. Cl. ......................................... 73/641
(58) Field of Classification Search .................... 73/625, 73/626, 628, 641
See application file for complete search history.

(56) References Cited

U.S. PATENT DOCUMENTS

| 4,760,351 | A | * | 7/1988 | Newell et al. .................... 331/48 |
| 5,744,902 | A | * | 4/1998 | Vig ................................. 310/360 |
| 6,236,951 | B1 | | 5/2001 | Payne et al. |
| 6,314,791 | B1 | * | 11/2001 | Rapp et al. .................... 73/24.06 |
| 7,117,743 | B2 | * | 10/2006 | Blakley ........................... 73/602 |
| 7,170,213 | B2 | * | 1/2007 | Yamanaka et al. ......... 310/313 R |
| 7,247,969 | B2 | * | 7/2007 | Nakaso et al. ............. 310/313 R |
| 7,362,034 | B2 | * | 4/2008 | Nakaso et al. ............. 310/313 A |
| 7,368,847 | B2 | * | 5/2008 | Nakaso et al. ............. 310/313 R |
| 7,368,848 | B2 | * | 5/2008 | Nakaso et al. ............. 310/313 R |
| 7,408,285 | B2 | * | 8/2008 | Nakaso et al. ............. 310/313 R |
| 7,423,360 | B2 | * | 9/2008 | Nakaso et al. ............. 310/313 R |
| 8,113,063 | B2 | * | 2/2012 | Nakaso ........................... 73/861 |
| 2005/0016276 | A1 | * | 1/2005 | Guan et al. ..................... 73/579 |
| 2005/0022601 | A1 | | 2/2005 | Blakley |
| 2009/0124513 | A1 | * | 5/2009 | Berg et al. ......................... 506/9 |
| 2010/0288014 | A1 | * | 11/2010 | Yao et al. ..................... 73/24.06 |

FOREIGN PATENT DOCUMENTS

| JP | 2000-500861 | 1/2000 |
| JP | 2002-243609 | 8/2002 |
| JP | 2005-10098 | 1/2005 |
| JP | 2005-55430 | 3/2005 |
| JP | 2005-333457 | 12/2005 |
| JP | 2007-233816 | 9/2007 |

OTHER PUBLICATIONS

Kenji Aoki et al., "Study of Odor Sensor using Ball SAW Devices," National Convention Record I.E.E. Japan, vol. 2006, No. 3, Mar. 15, 2006, 2 pages.
Kenji Aoki et al., "Study of Odor Sensor using Ball SAW Device," IEICE Technical Report, vol. 105, No. 440 (US2005 82-92), Nov. 23, 2005, pp. 13-18.
International Search Report for PCT/JP2008/065902, mailed on Dec. 16, 2008.
English Translation of the International Preliminary Report on Patentability mailed Apr. 15, 2010 in corresponding International Patent Application PCT/JP2008/065902.

* cited by examiner

*Primary Examiner* — Peter J Macchiarolo
*Assistant Examiner* — Rose M Miller

(57) ABSTRACT

The elastic wave measurement apparatus, when a high-frequency burst signal is input to the first ball SAW device, an input destination of the high-frequency burst signal is switched in sequence to another one of the ball SAW devices before a detection time at which an output signal from the first ball SAW device is detected, and at and after the detection time, output signals of the response characteristics of those ball SAW devices from the first ball SAW device to the last ball SAW device are detected in sequence.

28 Claims, 5 Drawing Sheets

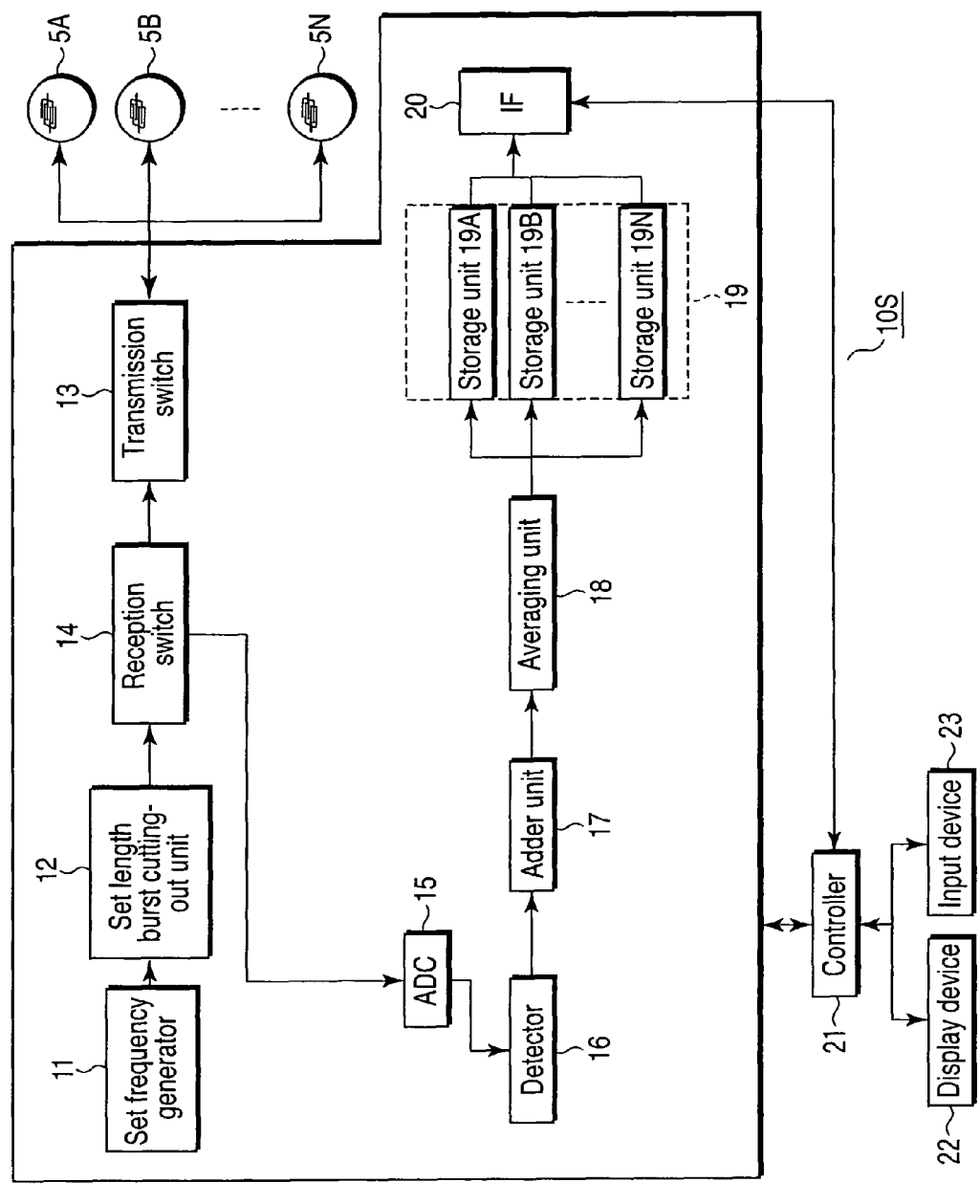
F I G. 4

ELASTIC WAVE MEASUREMENT APPARATUS AND METHOD

CROSS-REFERENCE TO RELATED APPLICATIONS

This application is a U.S. Continuation Application claiming priority benefit under 35 U.S.C. Section 111(a), of PCT International Application No. PCT/JP2008/065902, filed Sep. 3, 2008, which claims earlier priority benefit to Japanese Application No. 2007-243073, filed Sep. 19, 2007, the entire disclosures of which are incorporated by reference as a part of this application.

This application is based upon and claims the benefit of priority from prior Japanese Patent Application No. 2007-243073, filed Sep. 19, 2007, the entire contents of which are incorporated herein by reference.

BACKGROUND OF THE INVENTION

1. Field of the Invention

The present invention relates to an elastic wave measurement apparatus capable of measuring, at a high speed, response characteristics of a plurality of elastic wave devices to which a high-frequency signal from a single high-frequency signal generation means is input.

2. Description of the Related Art

In recent years, various types of sensors are developed by using elastic wave devices.

Examples of the elastic wave device include a SAW device configured to excite a surface acoustic wave (hereinafter referred to also as a SAW), and device utilizing a quartz crystal microbalance (hereinafter referred to also as a QCM).

A SAW device configured to excite a surface acoustic wave is provided with a piezoelectric substance and comb-like electrode. The piezoelectric substance is a material in which a strain is caused when an impulse signal or high-frequency burst signal is applied thereto, and crystal, langasite or the like is used as the piezoelectric substance. Examples of the SAW device include, as representatives, a device obtained by forming a piezoelectric substance into a flat shape, and device obtained by forming the piezoelectric substance into a spherical shape, which is a spherical surface acoustic wave device (hereinafter referred to also as a ball SAW device).

The flat SAW device is provided with comb-like electrodes at both ends of the piezoelectric substance. In the flat SAW device, when an input signal is applied to the comb-like electrode at one end thereof, a surface acoustic wave of an ultrasonic wave is produced. Further, when the surface acoustic wave propagates to the comb-like electrode at another end thereof, a voltage is produced in the comb-like electrode, thereby making it possible to acquire an output signal. Here, a frequency of the surface acoustic wave is determined by the elastic constant of the base material, and interval between the comb-like electrodes. Accordingly, such a SAW device is used mainly as a small-sized RF filter.

Further, there is a type of flat SAW device in which a comb-like electrode is arranged in the vicinity of a center of the propagation path, and reflectors are provided at positions on the right and left opposed to each other. According to this type of flat SAW device, the surface acoustic wave excited at the comb-like electrode is reflected by the reflectors, and goes back and forth past the comb-like electrode. Further, when the surface acoustic wave passes the comb-like electrode, an output signal is acquired. Here, while the surface acoustic wave repeats the round trip, i.e., while the wave makes the first round trip, second round trip, . . . , if a substance adheres on the propagation path, the velocity of the surface acoustic wave changes. Thus, by measuring a change in the velocity of the surface acoustic wave, application of the SAW device to various types of sensors is enabled.

In the ball SAW device, the piezoelectric substance is formed into a spherical shape, and a comb-like electrode is arranged on the propagation path of the ultrasonic wave. When an impulse signal or high-frequency burst signal is applied to the comb-like electrode of the ball SAW device, a surface acoustic wave is produced on the surface of the piezoelectric substance. The surface acoustic wave goes around the spherical piezoelectric substance, and returns to the original comb-like electrode. At the comb-like electrode, a high-frequency RF signal can be acquired. Further, the surface acoustic wave on the surface of the piezoelectric substance continues to go around the substance, and makes multiple circuits such as 10, 20 . . . 100 circuits, . . . Owing to the above characteristics, it is possible for the ball SAW device to take a longer propagation distance than the flat SAW device in spite of the size thereof smaller than the flat SAW device. Further, the ball SAW device includes no reflector, and hence the loss in the ball SAW device is small. Accordingly, it is possible to utilize the ball SAW device not only as a high-frequency filter, but also as a high-sensitivity sensor.

In the ball SAW device, for example, when the surface acoustic wave goes around the propagation path of the piezoelectric substance, if a substance adheres on the propagation path, the velocity or intensity of the surface acoustic wave is lowered by the mass-loading effect, or, depending on the adhering substance, the surface on the propagation path is hardened, whereby the velocity of the surface acoustic wave is increased, or the intensity thereof is changed. Further, even if a substance does not adheres to the surface of the propagation path, by a change in the atmosphere around the propagation path, the lost amount of energy of the surface acoustic wave changes, and hence the velocity or intensity thereof changes. Accordingly, by observing a change in the velocity or intensity of the surface acoustic wave, it is possible to detect whether or not a substance has adhered on the propagation path. Here, although a drop in velocity or intensity for one circuit is very small, when the number of circuits is increased, the change is also increased. As a result of this, in the ball SAW device, it is possible to make the propagation distance of the surface acoustic wave long, and hence it is possible to detect the adhering substance at high sensitivity (see, for example, Jpn. Pat Appln. KOKAI Publication No. 2005-333457).

Further, by forming, in advance, a film into which a specific substance is absorbed (hereinafter referred to as a sensitive film) on the propagation path of the surface acoustic wave, it becomes possible to specify the adhering substance.

Furthermore, by increasing the number of types of sensitive films, it becomes possible to simultaneously specify a plurality of types of substances, this being applicable to a gas sensor, odor sensor, and the like. However, the sensitive films are formed for each ball SAW device, and hence a plurality of ball SAW devices are required to examine a plurality of types of substances.

It should be noted that measuring the intensity of an output signal from a spherical surface acoustic wave device is nothing but observing an attenuation factor of the surface acoustic wave in the process in which the surface acoustic wave makes a circuit. Further, it is possible to obtain the attenuation factor from a change in the intensity of the surface acoustic wave concomitant with the propagation of the surface acoustic wave.

It should be noted that the term 'phase' used for a high-frequency signal generally means, when a predetermined time is defined, a temporal position of the corresponding signal at the defined time. Phase measurement in the output measurement of the spherical surface acoustic wave device generally refers to measuring a temporal position (phase) of a high-frequency output signal from the spherical surface acoustic wave device at the time at which a predetermined time has elapsed from the time at which the surface acoustic wave is excited by using Fourier analysis, quadrature detection, or wavelet transformation. Further, measuring the propagation (circling) velocity of the surface acoustic wave directly from the above measurement, or, obtaining the time at which, for example, the spherical surface acoustic wave device has finished outputting a predetermined number of times (the time at which the spherical surface acoustic wave device has finished circling a predetermined number of times), and obtaining a temporal distance from the circling start time at the obtained time is also called "measuring the phase". By measuring the phase in the manner described above, information on the propagation (circling) velocity of the surface acoustic wave is acquired in some cases.

BRIEF SUMMARY OF THE INVENTION

As described above, for the purpose of application to various sensors and the like, a plurality of surface acoustic wave devices are simultaneously used in some cases. Here, in general, even when response characteristics of a plurality of elastic wave devices are measured, a plurality of high-frequency signal generation means are not used, and a single high-frequency signal generation means is used. This is for the following reason. Without using a single high-frequency signal generation means, it is not possible to obtain synchronization between measurement processing timings of the respective surface acoustic wave devices, or synchronization of the timing to be used as a point of reference of the phase measurement with the detection means is not obtained, and hence time series measurement or phase measurement is made difficult.

However, when the response characteristics of a plurality of elastic wave devices are measured by using a single high-frequency signal generation means, the time required to excite elastic waves is prolonged in accordance with the number of elastic wave devices.

The present invention has been contrived in view of these circumstances, and provides an elastic wave measurement apparatus capable of measuring, at a high speed, response characteristics of a plurality of elastic wave devices to which a high-frequency signal from a single high-frequency signal generation means is input.

The present invention takes the following measures to solve the above-mentioned problem.

According to an embodiment of the invention, an elastic wave measurement apparatus configured to measure response characteristics from a plurality of elastic wave devices configured to excite elastic waves in accordance with input of a high-frequency signal, comprises:

single high-frequency signal generation means for generating the high-frequency signal;

input means for inputting the high-frequency signal to each of the elastic wave devices;

switching means for, when the high-frequency signal is input to the first elastic wave device, switching in sequence the input destination of the high-frequency signal to another one of the elastic wave devices before the detection time at which an output signal from the first elastic wave device is detected;

detection means for, at and after the detection time, detecting in sequence output signals of response characteristics of those elastic wave devices from the first elastic wave device to the last elastic wave device; and measurement means for measuring elastic waves excited at each of the elastic wave devices on the basis of the output signals detected by the detection means.

According to another embodiment of the invention, the measurement means measures a phase of the elastic wave excited at each of the elastic wave devices.

According to a still another embodiment of the invention, the measurement means measures an intensity of the elastic wave excited at each of the elastic wave devices.

According to a still another embodiment of the invention, the measurement means simultaneously measures a phase and an intensity of the elastic wave excited at each of the elastic wave devices.

According to a still another embodiment of the invention, the measurement means measures a delay time of the elastic wave excited at each of the elastic wave devices for a reference time.

According to a still another embodiment of the invention, the elastic wave measurement apparatus further comprises averaging means (18) for repetitively executing input of the high-frequency signal to those elastic wave devices from the first elastic wave device to the last elastic wave device averaging times of a number set in advance, and averaging the output signals from the elastic wave devices or measurement values.

According to a still another embodiment of the invention, when the output signal from the elastic wave device is an analog signal, the detection means detects the output signal after converting the analog signal into a digital signal.

According to a still another embodiment of the invention, the switching means switches the input destination of the high-frequency signal to the elastic wave devices from one to another of the devices at predetermined time intervals.

According to a still another embodiment of the invention, when a time at which the input destination of the high-frequency signal to the elastic wave devices is switched from one to another of the devices, and a time at which the output signal from one of the elastic wave devices is detected coincide with each other, the switching means stands by to input the high-frequency signal.

According to a still another embodiment of the invention, the elastic wave device is a surface acoustic wave device in which a surface acoustic wave is excited on a surface of a piezoelectric substance.

According to a still another embodiment of the invention, the piezoelectric substance is provided with a cylindrical surface, and includes a circling path along which the surface acoustic wave excited on the cylindrical surface circles.

According to a still another embodiment of the invention, the elastic wave device is a spherical surface acoustic wave device in which a piezoelectric substance is formed into a spherical shape, and includes a circling path along which the excited surface acoustic wave circles.

According to a still another embodiment of the invention, the input means inputs the high-frequency signal to each of the elastic wave devices in such a manner that the surface acoustic wave becomes shorter than the circling time in which the surface acoustic wave makes a circuit along the circling path.

According to a still another embodiment of the invention, an elastic wave measurement method used for an elastic wave measurement apparatus comprising a plurality of elastic wave devices configured to output response characteristics of elastic waves in accordance with input of a high-frequency signal, a single high-frequency signal generation means for generating the high-frequency signal, and switching means for inputting the high-frequency signal generated by the high-frequency signal generation means to each of the elastic wave devices by switching in sequence the input to each of the elastic wave devices, the method comprises:

an input step of inputting the high-frequency signal to a first elastic wave device;

a switch step of inputting, after inputting the high-frequency signal to the first elastic wave device, the high-frequency signal to one of the elastic wave devices by switching in sequence an input destination of the high-frequency signal to another one of the elastic wave devices before a detection time at which an output signal from the first elastic wave device is detected;

a detection step of detecting, at and after the detection time, in sequence output signals of response characteristics of those elastic wave devices from the first elastic wave device to a last elastic wave device; and a measurement step of measuring elastic waves excited at each of the elastic wave devices based on the output signals detected by the detection step.

According to a still another embodiment of the invention, in the detection step, a phase of the elastic wave excited at each of the elastic wave devices is measured.

According to a still another embodiment of the invention, in the measurement step, an intensity of the elastic wave excited at each of the elastic wave devices is measured.

According to a still another embodiment of the invention, in the measurement step, a phase and an intensity of the elastic wave excited at each of the elastic wave devices are simultaneously measured.

According to a still another embodiment of the invention, in the measurement step, a delay time of the elastic wave excited at each of the elastic wave devices for a reference time is measured.

According to a still another embodiment of the invention, the elastic wave measurement method further comprises an averaging step of repetitively executing a processing from the input step to the measurement step averaging times of a number set in advance, and averaging the output signals from the elastic wave devices or measurement values.

According to a still another embodiment of the invention, in the detection step, when the output signal from the elastic wave device is an analog signal, the output signal is detected after the analog signal is converted into a digital signal.

According to a still another embodiment of the invention, in the switch step, the input destination of the high-frequency signal to the elastic wave devices is switched from one to another of the devices at predetermined time intervals.

According to a still another embodiment of the invention, in the switch step, when a time at which the input destination of the high-frequency signal to the elastic wave devices is switched from one to another of the devices, and a time at which the output signal from one of the elastic wave devices is detected coincide with each other, input of the high-frequency signal is made on standby.

According to a still another embodiment of the invention, the elastic wave device is a surface acoustic wave device in which a surface acoustic wave is excited on a surface of a piezoelectric substance.

According to a still another embodiment of the invention, in the elastic wave device, the piezoelectric substance is provided with a cylindrical surface, and includes a circling path along which the surface acoustic wave excited on the cylindrical surface circles.

According to a still another embodiment of the invention, the elastic wave device is a spherical surface acoustic wave device in which a piezoelectric substance is formed into a spherical shape, and includes a circling path along which the excited surface acoustic wave circles.

According to a still another embodiment of the invention, in the input step, the high-frequency signal is input to each of the elastic wave devices in such a manner that the surface acoustic wave becomes shorter than the circling time in which the surface acoustic wave makes a circuit along the circling path.

BRIEF DESCRIPTION OF THE SEVERAL VIEWS OF THE DRAWING

FIG. 4 is a schematic view showing the configuration of a general elastic wave measurement apparatus 10S.

DETAILED DESCRIPTION OF THE INVENTION

An embodiment of the present invention will be described below with reference to the accompanying drawings.

First Embodiment

Configuration of Elastic Wave Measurement Apparatus

Figure 1:
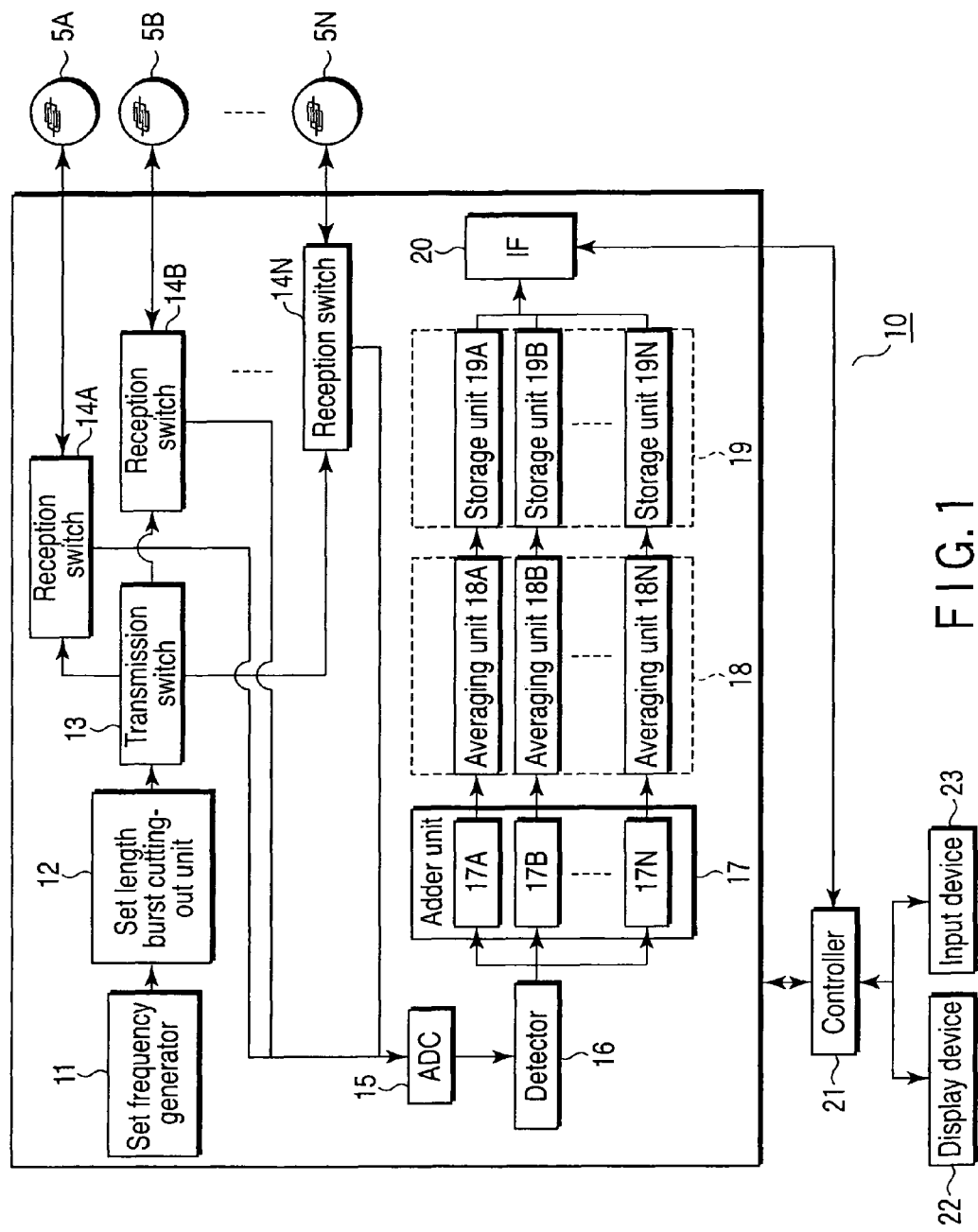
FIG. 1 is a schematic view showing the configuration of an elastic wave measurement apparatus 10 according to a first embodiment of the present invention.

FIG. 1 is a schematic view showing the configuration of an elastic wave measurement apparatus 10 according to a first embodiment of the present invention.

The elastic wave measurement apparatus 10 is an apparatus configured to measure response characteristics of a plurality of elastic wave devices exciting elastic waves in accordance with input of a high-frequency signal. In this embodiment, ball SAW devices 5A to 5N are used as elastic wave devices. By using the plurality of ball SAW devices 5A to 5N, it is possible to use units for a gas sensor configured to distinguish a plurality of types of gases from each other for measurement, odor sensor, and the like. In order to distinguish the types of gases or odors from each other, it is general to form sensitive films on the surface of the device. Besides, the ball SAW device can be used as a thermometer, pressure gauge, and the like. Further, by using a material configured to selectively absorb a physiological substance such as an antibody or the like as the sensitive film, the ball SAW device can be used also as a biosensor. It should be noted that each of the ball SAW devices 5A to 5N includes, on the surface of a spherical piezoelectric substance, a circling path along which a surface acoustic wave can circle.

The elastic wave measurement apparatus 10 is provided with a set frequency generator (high-frequency signal generation means) 11, a set length burst cutting-out unit 12, a transmission switch (switching means) 13, reception switches 14A to 14N, an analog-to-digital converter (ADC) 15, a detector 16, an adder unit 17, averaging units 18A to 18N, storage units 19A to 19N, an interface 20, a controller 21, a display device 22, and an input device 23.

The set frequency generator 11 is a unit configured to excite a target frequency matched with the characteristics of the ball SAW device. Here, a single set frequency generator 11 generates a high-frequency signal.

The set length burst cutting-out unit 12 is a switch configured to cut out a high-frequency signal excited by the set frequency generator 11 for each arbitrarily determined time length. A high-frequency burst signal is generated by the set length burst cutting-out unit 12. Further, the set length burst cutting-out unit 12 adjusts the time length corresponding to the cut-out high-frequency signal in such a manner that the time length becomes shorter than the circling time in which the surface acoustic wave makes a circuit along the circling path. As a result of this, it is possible to separate, in terms of time, the signals repetitively output from the ball SAW devices 5A to 5N from each other.

It should be noted that although the burst signal is formed by the combination of the set frequency generator 11 and set length burst cutting-out unit 12, it is known to the public that not by cutting out a continuously generated signal, but by directly generating a signal which is digitally defined by the duration time, phase, and intensity by an operation of a large scale integrated circuit (LSI) itself operating on a predetermined clock, the same function can be imparted to the elastic wave measurement apparatus, this not being excluded from the present invention.

Further, in the present invention, the description will be given on the assumption that the above units take their roles. It is also known to the public that these units are contained in one LSI chip, this not being excluded from the present invention.

The transmission switch 13 is a unit configured to input the high-frequency burst signal obtained by the set length burst cutting-out unit 12 to the ball SAW devices 5A to 5N while sequentially switching the signal to one of the ball SAW devices 5A to 5N. Here, the transmission switch 13 switches in sequence the input destination of the high-frequency burst signal while spending a time longer than the circling time in which the surface acoustic wave makes a circuit along the propagation path on the ball SAW device 5. Giving a supplementary explanation, the switching timing of the input destination of the high-frequency burst signal, and size of the diameter of the piezoelectric substance of the ball saw device 5 are proportional to each other. Accordingly, in the case where the piezoelectric substance of the ball SAW device 5 is a crystal sphere with a diameter of 1 mm, when the frequency of the high-frequency burst signal is 150 MHz, the transmission switch 13 switches the input destination by spending a time of 1 μs or longer. Further, when the diameter is 3.3 mm, the transmission switch 13 switches the input destination after an elapse of a time longer than 3.3 μs.

It should be noted that when the time at which the input destination of the high-frequency burst signal is switched from one to another of the ball SAW devices 5A to 5N, and time at which an output signal from one of the ball SAW devices 5A to 5N is detected coincide with each other, the transmission switch 13 stands by to input the high-frequency burst signal. As a result of this, it is possible, in general, to prevent an input signal with a large voltage value from being added to an output signal as noise, and hence it is possible to detect the output signal with a high degree of accuracy.

The reception switches 14A to 14N are provided to each of the ball SAW devices 5A to 5N, and are configured to extract a circling signal of a surface acoustic wave excited at each of the ball SAW devices 5A to 5N. Here, each of the reception switches 14A to 14N extracts a circling signal of the 100th circuit from each of the ball SAW devices 5A to 5N as a signal to be analyzed. The extracted circling signal is sent to the analog-to-digital converter 15 as an output signal from each of the ball SAW devices 5A to 5N. It should be noted that the above 100th circuit is an example, and the number of circling times of the object to be measured is set in accordance with the characteristics of the ball SAW device.

The analog-to-digital converter (ADC) 15 is a unit configured to convert an analog output signal into a digital signal. This analog signal includes a signal a frequency of which is down-converted by using heterodyne detection for output signal from the ball SAW devise 5.

It should be noted that high-frequency burst signals are input to the respective ball SAW devices 5A to 5N by the transmission switch 13 with a time lag. Accordingly, output signals from the respective SAW devices 5A to 5N are input to the analog-to-digital converter 15 in accordance with the switching time lag of the transmission switch 13. As a result of this, the output signals from the respective ball SAW devices 5A to 5N are separated from each other in terms of time, and hence it is sufficient to use only one analog-to-digital converter 15.

The detector 16 is a unit configured to convert an output signal digitized by the analog-to-digital converter 15 into data of the phase and intensity. Further, the detector 16 is also provided with a calculation function to be used when the above digitized output signal is converted into data of the phase and intensity.

The adder unit 17 is a unit configured to add the phase data and intensity data calculated by the detector 16 together. This adder unit 17 includes storage areas 17A to 17N corresponding to the ball SAW devices 5A to 5N, and temporarily stores added data in the storage areas 17A to 17N. Further, the adder unit 17 is also provided with a function of calculating data.

The averaging units 18A to 18N each include a function of calculating data, and are configured to average output signals from the ball SAW devices 5A to 5N when input of a high-frequency burst signal to those ball SAW devices from the first ball SAW device 5A to the last ball SAW device 5N has been repetitively executed the "averaging times" of a number set by the controller 21 to be described later. More specifically, each of the averaging units 18A to 18N averages the data obtained by adding the phase data and intensity data together by the adder unit 17.

Giving a supplementary explanation, in the measurement of the response characteristics of the ball SAW device 5, the influence of noise cannot be eliminated by only one time measurement, and data is measured a plurality of times. That is, when measurement data of the nth ball SAW device 5N is stored, measurement is started again from the first ball SAW device 5A. However, when, at and after the second time, the first ball SAW device 5A is measured, it is necessary that the measurement be carried out after the influence of the circling of the surface acoustic wave excited last time has been lost. More specifically, when a high-frequency burst signal of 150 MHz is input to a ball SAW device of a crystal sphere with a diameter of 1 mm, waiting time of 1 ms or more is sufficient.

It should be noted that although the elastic wave measurement apparatus 10 may be configured in such a manner that data items from the respective ball SAW devices 5A to 5N are averaged by a plurality of averaging units 18A to 18N, the apparatus 10 may also be configured in such a manner that data items from each of the ball SAW devices 5A to 5N are averaged in sequence by a single averaging unit 18.

The storage units 19A to 19N are configured to store data averaged by the averaging units 18A to 18N in such a manner that data items respectively averaged by the averaging units 18A to 18N correspond to the ball SAW devices 5A to 5N. Further, each of the storage units 19A to 19N includes an area configured to store incidental data in addition to the phase data and intensity data from each of the ball SAW devices 5A to 5N. It should be noted that here, although the plurality of storage units 19A to 19N are used to correspond to the respective ball SAW devices 5A to 5N, a single storage unit 19 in which respective data items are classified according to the addresses to be stored may be used. Further, the storage unit may also be configured to store data in sequence, and to be able to transmit data to an external personal computer (PC) and the like.

The interface (IF) 20 enables a relay of data from the above-mentioned units 11 to 19 to the controller 21 controlling the overall elastic wave measurement apparatus 10. More specifically, the interface 20 conforms to USB, Ethernet (trade name), Bluetooth (trade name), IEEE-1394, PHS, WCDMA, CDMA2000, IEEE-802.xx or the like, and enables transfer of data irrespectively of whether the data is of the wired system or wireless system. Further, the interface 20 enables communication to be carried out when the apparatus 10 operates to be linked with another elastic wave measurement apparatus 10.

The controller 21 is a computer configured to control the overall elastic wave measurement apparatus 10, carries out frequency control of the high-frequency burst signal, adjustment of the burst signal length, switching control of the transmission switch 13, switching control of reception switches 14A to 14N, and the like, and start the response measurement of the elastic wave by carrying out the measurement program.

More specifically, when the high-frequency signal is input to the first ball SAW device 5A, the controller 21 controls the transmission switch 13 in such a manner that the input destination of the high-frequency signal is switched in sequence to another one of the ball SAW devices 5B to 5N before an output signal from the first ball SAW device 5A is detected.

Further, the controller 21 sets the "number of averaging times" and controls the calculation of the averaging units 18A to 18N. Thereafter, the controller 21 measures the response characteristics of the surface acoustic wave excited at each of the ball SAW devices 5A to 5N on the basis of the output signal averaged by each of the averaging units 18A to 18N.

Furthermore, the controller 21, although it is operable by itself alone, carries out communication with another computer, control of the display device 22, reception of input data from the input device 23, error processing of an input numerical value, and the like. Besides, the controller 21 is provided with functions of extracting data, storing the data in an external storage unit, managing the stored data, preparing a report, and disclosing the measurement results to the Internet and the like. Further, when a plurality of elastic wave measurement apparatuses 10 is prepared, the controller 21 is also provided with a function of controlling the apparatuses in an integrative manner.

The display device 22 is a general display or touch panel display, and displays the state of the elastic wave measurement apparatus 10, task state, and the like.

The input device 23 is constituted of a general keyboard, mouse, dedicated input device, above-mentioned touch panel display, and the like, and enables input of various setting values of the elastic wave measurement apparatus 10, frequency of the burst signal, burst length, averaged number of times, and the like.

(Operation of Elastic Wave Measurement Apparatus)

Figure 2:
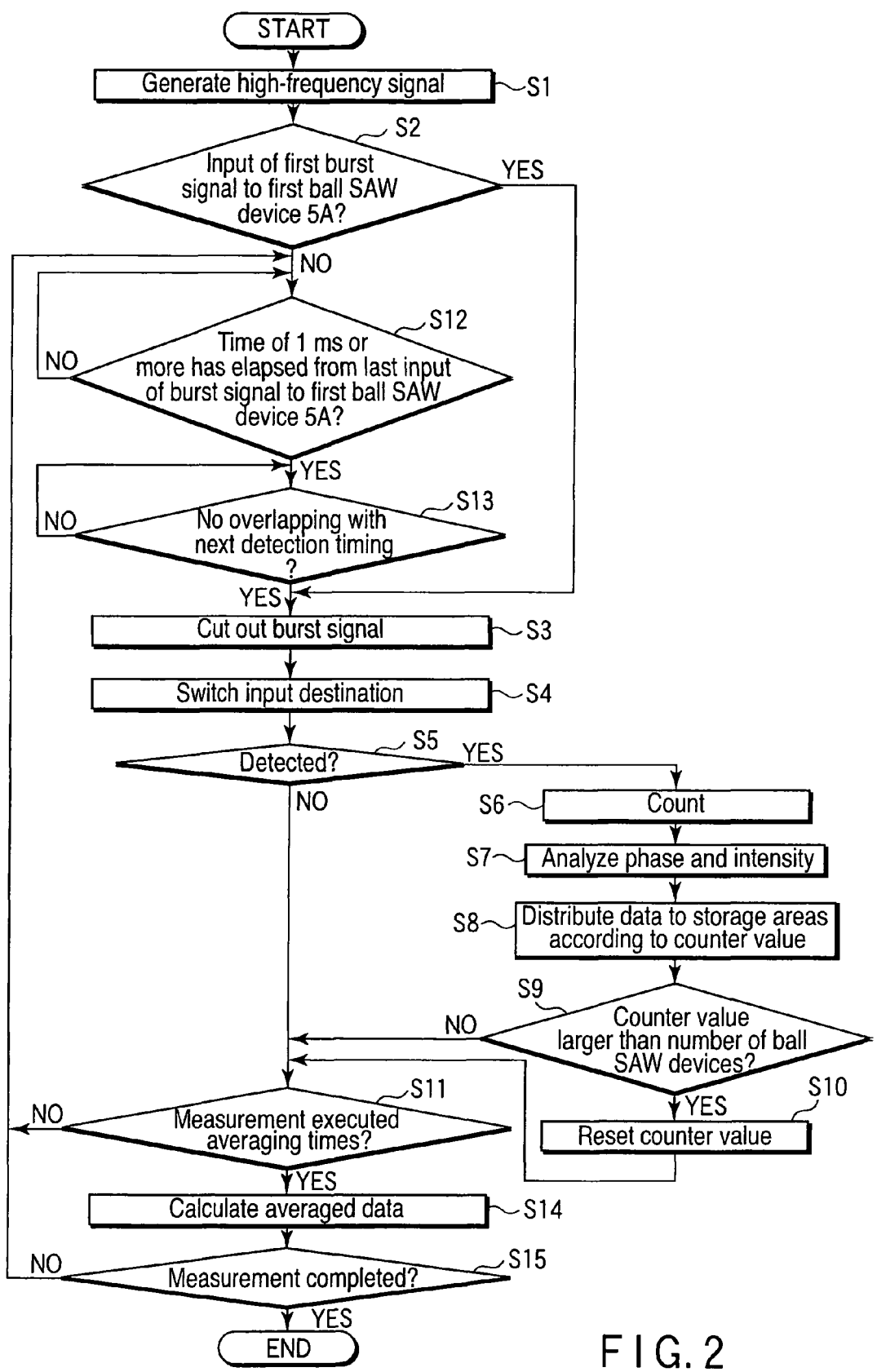
FIG. 2 is a flowchart used to explain an operation of the elastic wave measurement apparatus 10 according to the embodiment.
Figure 3:
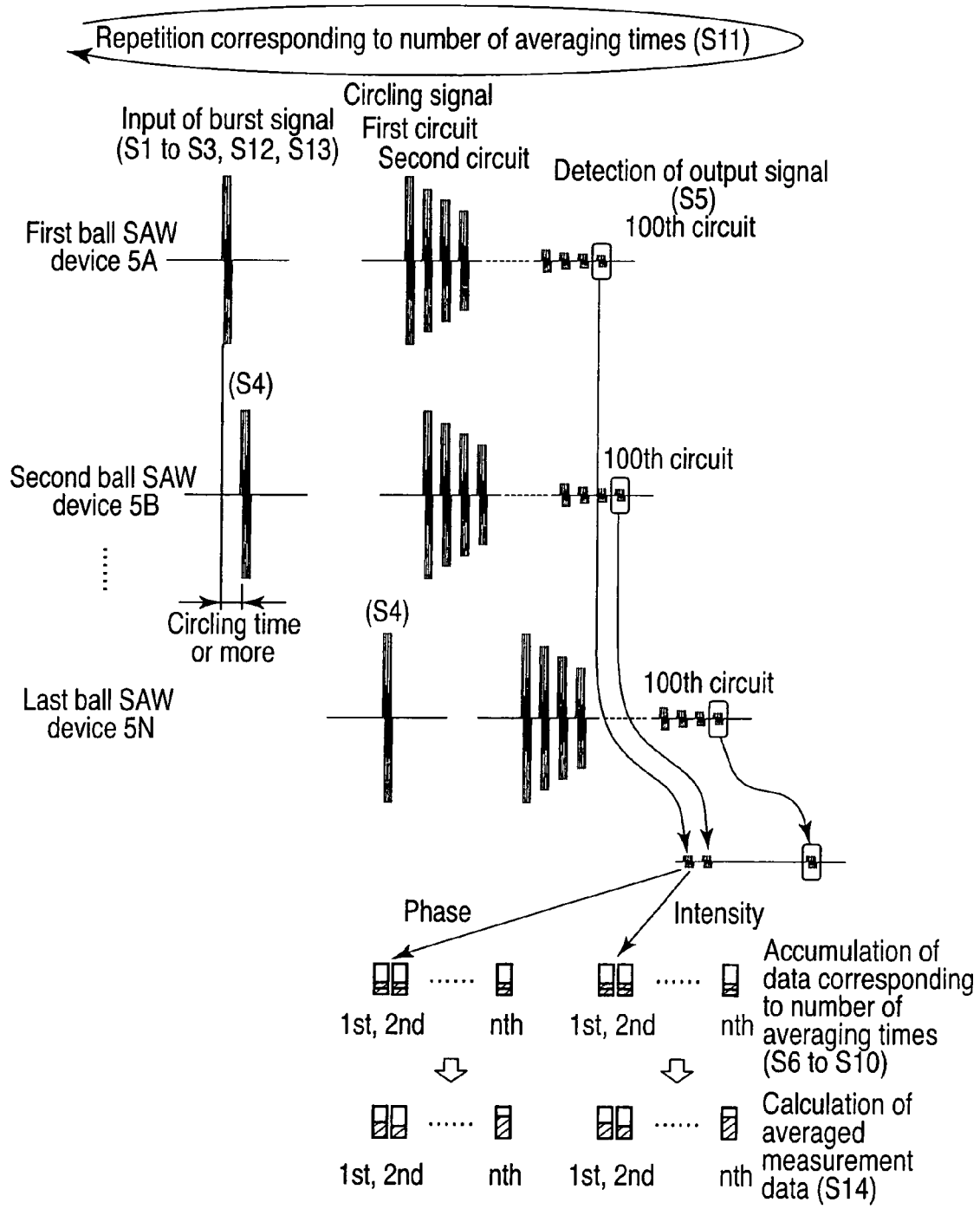
FIG. 3 is a signal correlation diagram used to explain the operation of the elastic wave measurement apparatus 10 according to the embodiment.

Next, an operation of the elastic wave measurement apparatus 10 according to this embodiment will be described below by using the flowchart of FIG. 2 and signal correlation diagram of FIG. 3.

First, a high-frequency signal matched with the characteristics of the ball SAW devices 5A to 5N is generated by the set frequency generator 11 (step S1). Here, when the input to the first ball SAW device 5A is of the first time, a high-frequency burst signal for input is generated through the set length burst cutting-out unit 12 (YES in step S2, and step S3). It should be noted that in the set length burst cutting-out unit 12, a high-frequency burst signal is generated in such a manner that the burst signal becomes shorter than the circling time in which the surface acoustic wave makes a circuit along the circling path in order to separate the signals output from the respective ball SAW devices 5A to 5N in terms of time.

Then, the high-frequency burst signal is input to the first ball SAW device 5A through the transmission switch 13 and reception switch 14A.

Further, when the high-frequency burst signal is input to the first ball SAW device 5A, the input destination of the high-frequency signal is switched in sequence by the transmission switch 13 to another one of the ball SAW devices 5B to 5N (step S4). At this time, the input destination of the high-frequency burst signal is switched in sequence by the transmission switch 13 to another one of the ball SAW devices 5B to 5N before the detection time at which an output signal from the first ball SAW device 5A is detected.

When the high-frequency burst signal is input to, a surface acoustic wave is excited in the propagation path of each of the ball SAW devices 5A to 5N. The propagation path of each of the ball SAW devices 5A to 5N is a circling path, and hence the excited surface acoustic wave continues to circle along the propagation path.

Further, at and after the first detection time, output signals of the first ball SAW device 5A to the last ball SAW device 5N are detected in sequence through the reception switches 14A to 14N (YES in step S5). Here, the circling signal to be obtained when the surface acoustic wave has finished the 100th circuit is made the object of measurement, and hence the output signals are detected in sequence after an elapse of 100 μs from the input of the high-frequency burst signal to the first ball SAW device 5A.

In the detection step, after a counter value indicating the number of times of detection signals is counted (step S6), phase data and intensity data are obtained by the detector 16 from the output signal digitized by the analog-to-digital converter 15 (step S7). Further, on the basis of the counter value, data items are distributed to the data storage areas of the adder unit 17 (step S8). It should be noted that when the counter value exceeds the total number of ball SAW devices 5A to 5N, the value is reset (YES in step S9, and step S10). As a result of this, it becomes possible to associate the counter value and the respective ball SAW devices 5A to 5N with each other.

It should be noted that it is also possible to obtain the phase data and intensity data by using the quadrature detection (orthogonal detection) method. It is possible to obtain phase data and intensity data from a sine component and cosine component calculated from a signal obtained by digitizing an output signal to be measured by using the analog-to-digital converter.

After this, measurement of the response characteristics corresponding to the number of averaging times set in advance is carried out (NO in step S11).

It should be noted that a period of time of about 1 ms is required until the influence of the circling signal of the surface acoustic wave is lost, and hence measurement to be carried out for the second time and thereafter is carried out after an elapse of 1 ms or more from the previous measurement (step S12). That is, when, after the input to the first ball SAWA device 5A, input to the ball SAW device 5A is carried out again, the controller 21 determines whether or not 1 ms or more has elapsed from the previous input to the ball SAW device 5A, and if 1 ms or more has not elapsed yet (NO in step S12), the input is made to wait for 1 ms or more. Further, the controller 21 determines whether or not the timing at which the high-frequency burst signal is input to each of the ball SAW devices 5A to 5N overlaps the detection timing of step S5, and if the input timing overlaps the detection timing, the input timing is shifted in order that the input timing may not overlap the detection timing (step S13). Thereafter the flow is advanced to step S3. Here, the time required until the influence of the circling signal of the surface acoustic wave is lost is normally known from the number of ball SAW devices 15 to be measured, and the evaluation of the output of the devices, and hence the operation may also be carried out by a program in which the next measurement is made to wait for a predetermined time without carrying out the above-mentioned logical determination step.

When the processing of above steps S3 to S13 has been executed the averaging times of the predetermined number, an average value of measurement data for each of the ball SAW devices 5A to 5N is calculated by the averaging unit 17 (YES in step S11, and step S14). The calculated average values of the measurement data are stored in the storage units 9A to 9N provided in association with the respective ball SAW devices 5A to 5N.

Thereafter, the processing of above steps S3 to S14 is executed the measurement times of a number set in advance (step S15).

(Function/Advantage of Elastic Wave Measurement Apparatus)

As described above, in the elastic wave measurement apparatus 10 according to this embodiment, when the high-frequency burst signal is input to the first ball SAW device 5A, the input destination of the high-frequency burst signal is switched in sequence to another one of the ball SAW devices 5B to 5N before the detection time at which the output signal from the first ball SAW device 5A is detected, and at and after the first detection time, output signals of the response characteristics of those ball SAW devices from the first ball SAW device 5A to the last ball SAW device 5N are detected in sequence. Therefore, according to the elastic wave measurement apparatus 10, when the response characteristics of a plurality of ball SAW devices 5A to 5N to which a high-frequency signal from a single set frequency generator 11 is input are measured, it is possible to carry out the measurement at a higher speed than in the case where the response characteristic of one ball SAW device is measured, and thereafter the response characteristic of another ball SAW device is measured.

A description will be given below by taking a specific example.

It is assumed that the diameter of the ball SAW device is 1 mm, and switching timing of the transmission switch 13 is 1 μs. Further, it is assumed that measurement data items of 256 times are averaged to obtain one measurement data item. Further, an elastic wave measurement apparatus 10 stands by time of 1 ms not to be influenced by a previous circling for every measurement of one time.

Under such conditions, an output signal of the surface acoustic wave that has made 100 circuits along the propagation path of the ball SAW device is measured.

In the ball SAW device with a diameter of 1 mm, 1 μs is necessary for the surface acoustic wave to make a circuit along the propagation path. Here, when the transmission switch 13 switches the input destination every 1 μs, it becomes possible to switch the input destination to 1000 ball SAW devices during the waiting for 1 ms which is the time in which the influence of the circling of the surface acoustic wave excited last time is lost. Accordingly, when the average value of the measurement data items of 256 times is to be obtained, the time for the overall measurement becomes 256 ms (1 ms/time×256 times=256 ms), and the time necessary for one scanning operation becomes 256 ms.

On the other hand, a general elastic wave measurement apparatus 10S of the conventional system is configured as shown in FIG. 4. In FIG. 4, the same parts as those in FIG. 1 are denoted by the same reference symbols as those in FIG. 1 and, unless otherwise described, a duplicated explanation will be omitted. In such an elastic wave measurement apparatus 10S, after a high-frequency burst signal is input to one ball SAW device 5A, no high-frequency burst signal is input to another one of ball SAW devices 5B to 5N until an output signal from the ball SAW device 5A is obtained. Accordingly, when a single set frequency generator 11 is used, a period of time of 256 ms is required to obtain only one measurement data item of one ball SAW device.

Making a comparison between the above cases, according to the elastic wave measurement apparatus 10 associated with this embodiment, it is possible to obtain one measurement data item from each of the 1000 ball SAW devices within the same period of time of 256 ms. In other words, when one measurement data item is to be obtained from each of the 1000 ball SAW devices, it is possible to carry out measurement with one thousandth of the velocity required in the conventional elastic wave measurement apparatus 10S.

That is, as a method of measuring the propagation velocity of the surface acoustic wave, it is possible to carry out measurement in accordance with a method configured to measure the time at which a burst-like output signal exceeds a predetermined threshold, or employ a method configured to directly obtain the delay time by calculating a slight change of the position in the time axis of an output waveform by using wavelet transformation or the like.

It should be noted that in carrying out measurement of a surface acoustic wave, the delay time of the surface acoustic wave excited at each of the ball SAW devices 5A to 5N for the reference time may be measured. It is possible to obtain a change in amount or change in temperature of a substance adhered to the surface of the ball SAW device from the delay time.

Further, in the elastic wave measurement apparatus 10, input of the high-frequency signal to those ball SAW devices from the first ball SAW device 5A to the last ball SAW device 5N is repetitively executed the averaging times of a number set in advance, and the output signals from the respective ball SAW devices 5A to 5N are averaged. Accordingly, random noise is canceled out, and it is possible to provide an elastic wave measurement apparatus 10 of high accuracy.

Further, in each of the ball SAW devices 5A to 5N according to this embodiment, the piezoelectric substance is formed into a spherical shape, further a circling path of an excited surface acoustic wave is provided, and hence the propagation distance of the surface acoustic wave can be made long.

Accordingly, the elastic wave measurement apparatus 10 is capable of measurement of high accuracy.

It should be noted that, the ball SAW devices 5A to 5N according to this embodiment may also be configured in such a manner that the piezoelectric substance is provided with a cylindrical surface, and includes a circling path along which the surface acoustic wave excited on the cylindrical surface circles. In this case too, it is possible to prolong the propagation path of the surface acoustic wave, and hence the elastic wave measurement apparatus 10 is capable of measurement of high accuracy.

Further, in the elastic wave measurement apparatus 10 according to this embodiment, the high-frequency signal is input to the respective ball SAW devices 5A to 5N in such a manner that the high-frequency signal becomes shorter than the circling time in which the surface acoustic wave makes a circuit along the circling path, and hence it is possible to obtain output signals separated from each other in terms of time from each of the ball SAW devices 5A to 5N.

Further, in the elastic wave measurement apparatus 10 according to this embodiment, when the output signal from each of the ball SAW devices 5A to 5N is an analog signal, the analog signal is converted into a digital signal by the analog-to-digital converter 15 to be thereafter detected, and hence it is possible to easily carry out calculation of data, and the like.

It should be noted that in this embodiment, the transmission switch 13 may switch the input destination of the high-frequency signal to another one of the ball SAW devices 5A to 5N at predetermined time intervals. As a result of this, it is possible to execute efficient switching processing.

However, when the input destination is switched at predetermined time intervals, there occurs a case where the time at which the input destination of the high-frequency burst signal is switched to another one of the ball SAW devices 5A to 5N, and the time at which an output signal from one of the ball SAW devices 5A to 5N is detected coincide with each other. In such a case, the transmission switch 13 stands by to input the high-frequency burst signal. As a result of this, it is possible to prevent the output signal from not being detected because of the influence of the input signal, and hence it is possible to detect the output signal with high accuracy.

Example 1

Multi-Gas Sensor (Gas Detector)

The elastic wave measurement apparatus 10 according to this embodiment can be utilized as a multi-gas sensor.

When the elastic wave measurement apparatus 10 is utilized as a multi-gas sensor, a sensitive film is formed by applying an adsorptive material adsorbing a gas to the surface of the circling path of the ball SAW device. Here, a sensitive film configured to adsorb a plurality of types of gases cannot specify a gas, and hence one sensitive film is configured to adsorb only one type of gas. Accordingly, in order to detect a plurality of types of gases, it is necessary to prepare sensitive films of a number greater than or equal to the number of types of gases to be detected.

Further, the ball SAW device has strong temperature dependence, and hence it is necessary to prepare a ball SAW device including no sensitive film for the purpose of temperature calibration. For example, assuming that the number of types of gases to be detected is nine, ten ball SAW devices including the one for temperature calibration are necessary.

Here, a crystal sphere with a diameter of 1 mm is used as the ball SAW device. Further, the input signal is a burst signal of 150 MHz, burst length is 0.8 µs, number of averaging times is 256 times, circuit of the measurement circling number is the 100th circuit, and heterodyne detection system configured to convert the frequency is employed for detection. It should be noted that 1 ms is necessary for the surface acoustic wave made to circle around the ball SAW device to finish the circling. Further, it is assumed here that the ball SAW devices are arranged two-dimensionally or three-dimensionally.

With respect to such a ball SAW device, in the conventional elastic wave measurement apparatus 10S, measurement is carried out after waiting for the influence of the previous circling to be lost, and hence standby time of 1 ms is required each time the measurement is carried out. Further, in order to obtain one measurement data item, measurement data items of 256 times are averaged. That is, in order to obtain one averaged measurement data item for one ball SAW device, a period of time of 0.256 s (1 ms×256=0.256 s) is required. Accordingly, in order to obtain measurement data for 10 ball SAW devices, a period of 2.56 s (0.256 s/piece×10 pieces=2.56 s) is required. For this reason, in the conventional elastic wave measurement apparatus 10S, it is impossible to observe a change of 2.56 s or less occurring in each ball SAW device.

On the other hand, in the elastic wave measurement apparatus 10 of Example 1, the transmission switch 13 switches the input destination at timing of 100 µs. Accordingly, in the elastic wave measurement apparatus 10, it is possible to input an input signal to 10 ball SAW devices during a period of 1 ms in which the influence of the surface acoustic wave is lost. Further, the circling signal of the 100th circuit is observed, and hence in order to obtain one measurement data item for each of the 10 ball SAW devices, a period of 1 ms (100 µs×10=1 ms) is required. Thus, in order to obtain a data item formed by averaging data items of measurement of 256 times for each of the 10 ball SAW devices, a time of 0.256 s (1 ms×256=0.256 s) is required. As a result of this, when attention is paid to one ball SAW device, although a change of 0.256 s or less is unobservable, time resolution ten times as large as the conventional elastic wave measurement apparatus 10S is obtained.

This point becomes an important difference when the ball SAW device is utilized as a multi-gas sensor. That is, assuming that three types of gases out of nine types of gases to be detected flow to the ball SAW devices, and disappear within 1 s, in the gas sensor using the conventional elastic wave measurement apparatus 10S, the number of measurement times is approximately 3.9 times (1 s÷0.256 s≈3.9 times), and hence it is possible to obtain only one measurement data item at most from each of the three ball SAW devices. Since only one measurement data item is obtained, it is difficult even to determine whether or not the measurement data item itself is noise, and such a sensor is not equal to the use as a gas sensor.

Conversely, according to the elastic wave measurement apparatus 10 associated with this embodiment, it is possible to carry out measurement of 3.9 times (1 s÷0.256 s≈3.9 times) for each of 10 ball SAW devices, and hence it is possible to obtain 3 to 4 measurement data items from each of the 3 ball SAW devices. Thus, the gas sensor employing the elastic wave measurement apparatus 10 is higher in reliability than the gas sensor using the conventional elastic wave measurement apparatus 10S.

It should be noted that when 2 ball SAW devices each including the same sensitive film are provided, and the total number of ball SAW devices is 19, it is possible to detect the direction in which the gas has flowed to come by the reaction time lag. Further, 53 µs is suitable for the switching timing of the transmission switch 13 in this case. The larger the number of ball SAW devices each of which is provided with the same sensitive film, the easier the direction in which the gas flows is grasped.

Example 2

Remote Hydrogen Sensor

Figure 5:
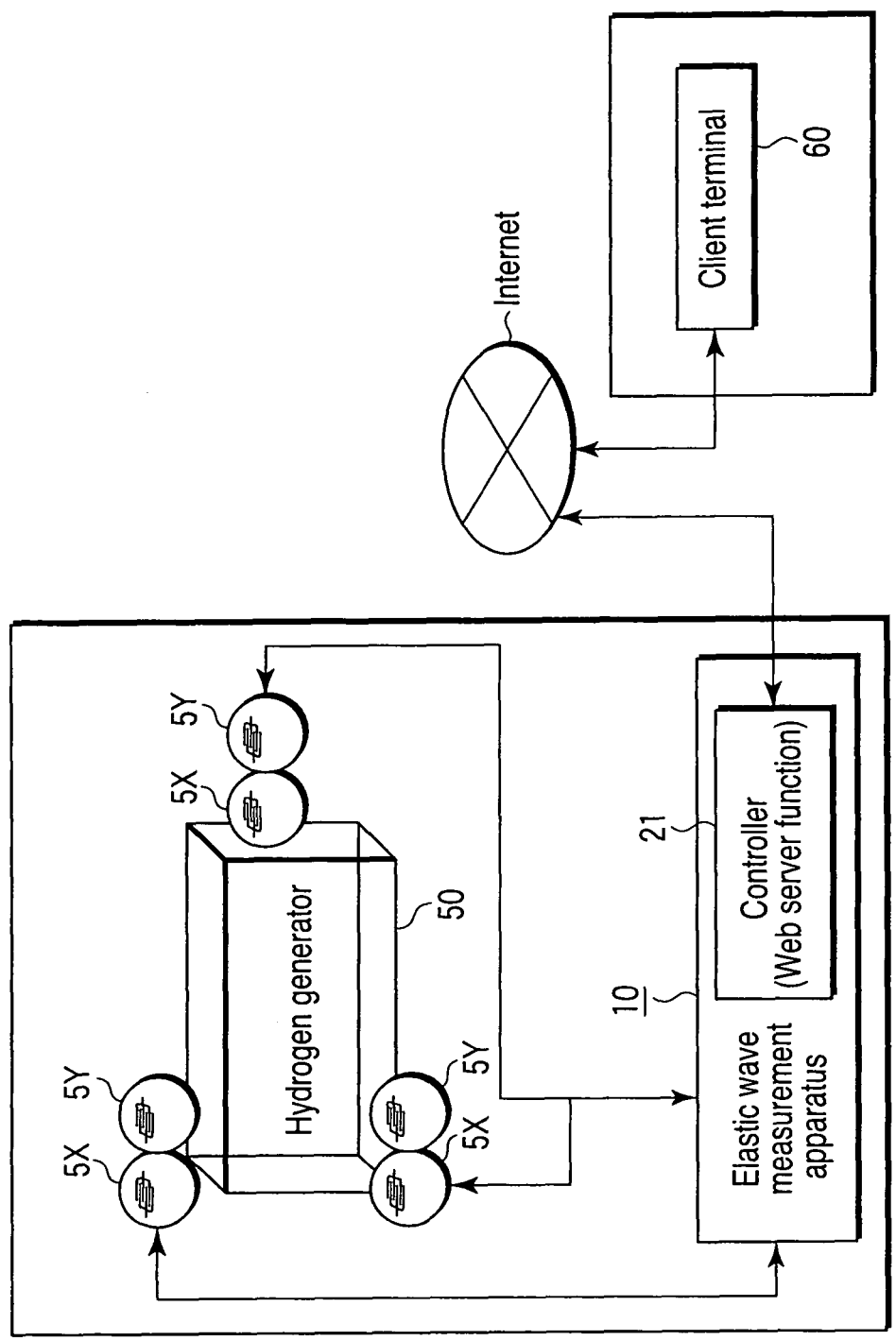
FIG. 5 is a schematic view showing the configuration of a remote hydrogen sensor.

The elastic wave measurement apparatus 10 according to this embodiment can be utilized as a remote hydrogen sensor. FIG. 5 is a schematic view showing the configuration of a remote hydrogen sensor according to this example.

In this example, it is assumed that there is an unattended room in which a hydrogen generator 50 is installed, and there are 100 points holding the possibility of hydrogen leakage in the hydrogen generator 50. Thus, a total of 200 ball SAW devices including 100 ball SAW devices 5X each including a sensitive film for hydrogen detection, and 100 ball SAW devices 5Y for temperature calibration of the devices 5X are arranged at the points holding the possibility of hydrogen leakage. It should be noted that the piezoelectric substance of the ball SAW device has a diameter of 1 mm.

Further, in this example, it is detected whether or not there is hydrogen leakage from a remote location. For that purpose, the elastic wave measurement apparatus 10 serves as a Web server, and transmits data to a client terminal 60 through the Internet. The respective ball SAW devices and elastic wave measurement apparatus 10 are connected to each other by wire or wireless. Measurement data from the ball SAW devices is sent to the controller 21 of the elastic wave measurement apparatus 10 at all times. The controller 21 graphs the measurement data, and transmits the graphed data to the client terminal 60. Further, when hydrogen leakage is detected, the controller 21 outputs an alert signal.

Here, a total of 200 ball SAW devices each having a diameter of 1 mm are arranged in the room to be monitored, and hence by setting switching timing of the transmission switch 13 at 5 µs (1 ms/200=5 µs), and setting the burst length at 0.8 µs, it is possible to obtain measurement data of each of the 200 ball SAW devices within 1 ms. Thus, assuming that the number of averaging times for the 100th circuit of the circling of the measurement object is 64, the time required to obtain one averaged measurement data item becomes 64 ms (1 ms×64=64 ms).

That is, according to the remote hydrogen sensor of this example, the ball SAW device is switched every 64 ms, and thus it is possible to monitor the overall hydrogen generator 50 in substantially real time.

The operation of the remote hydrogen sensor will be supplemented below. It is known to the public that an alloy of palladium and nickel is used for the sensitive film configured to detect hydrogen. In a state where remote hydrogen sensors are installed in the hydrogen generator 50, it is assumed that for example, hydrogen leaks from a part near, for example, the 51st ball SAW device. Here, the sensitive film has the property of becoming hard when it adsorbs hydrogen, and enhancing the sonic velocity, and hence the output signal from the ball SAW device 5X with a sensitive film arranged at the part exhibits a waveform of a surface acoustic wave with an enhanced velocity. Further, it is possible to observe a phenomenon in which attenuation of the surface acoustic wave is enlarged, and which is caused by the fact that the sensitive film adsorbs the energy of the surface acoustic wave, from the lowering of the intensity. Accordingly, the output signal from the ball SAW device 5X with the sensitive film exhibits a change that becomes larger in accordance with the hydrogen concentration, whereby it becomes possible to determine that hydrogen leaks. It should be noted that in the output signal from the ball SAW device 5Y for temperature calibration provided with no sensitive film, no change other than a change associated with the temperature is observed.

Further, hydrogen spreads all around, and drifts to the vicinity of the 50th and 52nd ball SAW devices arranged adjacent to the 51st ball SAW device. Further, the 50th and 52nd ball SAW devices also react in the same manner as the 51st ball SAW device. At this time, the sonic velocity and intensity of the surface acoustic wave change depending on the hydrogen concentration, and hence the respective ball SAW devices differ from each other in the rate of change with time.

Furthermore, when the ball SAW devices are arranged three-dimensionally, the sonic velocity and intensity differ in accordance with the hydrogen concentration, it is possible to observe at which part hydrogen leaks, and how the gas spreads. Further, it is possible to localize the part of hydrogen leakage, and hence it is possible to take prompt action when the hydrogen generator is repaired.

Further, the surface acoustic wave measurement apparatus is connected to the Internet, and hence it is possible to monitor the room from a remote location. It is further possible to safely confirm hydrogen leakage. It should be noted that the controller 21 is connected to the Internet, and thus it is possible to browse information through the Internet not only in the same building but also at a remote location.

It should be noted that in each of the plurality of elastic wave devices of the present invention, the base materials along which the surface acoustic waves propagate may not necessarily be formed separately from each other, and the surfaces along which the surface acoustic waves circle to propagate may not necessarily be separated from each other. It is sufficient if elastic waves or surface acoustic waves can be excited independently of each other in the respective elastic wave devices or surface acoustic wave devices. Further, it is evident from the gist of the present invention that elastic wave devices or surface acoustic wave devices sharing the base material or substrate serving as a propagation medium with each other may also be regarded as a plurality of elastic wave devices.

For example, in the spherical surface acoustic wave device, it is known that a plurality of, for example, about ten circling paths can be formed on a single spherical base material such as lithium niobate ($LiNbO_3$), lithium tantalate ($LiTaO_3$) or the like used as a piezoelectric crystalline base material, further it is also known that the same functions as a plurality of spherical surface acoustic wave devices can be formed on a single base material by forming an independent comb-like electrode on each of circling paths on the surface of the above-mentioned single spherical base material, and application to such a spherical surface acoustic wave device is not excluded from the present invention.

According to the present invention, it is possible to measure, at a high speed, response characteristics of a plurality of elastic wave devices to which a high-frequency signal from a single high-frequency signal generation means is input.

In the invention corresponding to claims 1 and 14, when the high-frequency signal is input to the first elastic wave device, the input destination of the high-frequency signal is switched in sequence to another one of the elastic wave devices before the detection time at which an output signal from the first elastic wave device is detected, further at and after the detection time, output signals of response characteristics of those elastic wave devices from the first elastic wave device to the last elastic wave device are detected in sequence, and hence when the response characteristics of a plurality of elastic wave devices to which the high-frequency signal from the single high-frequency signal generation means is input are measured, it is possible to provide an elastic wave measurement apparatus capable of measuring the response characteristics at a higher speed than an elastic wave measurement apparatus configured to measure the response characteristics of one elastic wave device, and then measure the response characteristics of another elastic wave device.

In the invention corresponding to claims 2, and 15, in addition to the function corresponding to claims 1 and 14, the measurement means measures the phase of the elastic wave excited at each of the elastic wave devices, and hence it is possible to obtain the temperature change from the amount of a substance adhered to the surface of the elastic wave device, change in modulus of elasticity of the sensitive film, and temperature dependence of the elastic wave device on the basis of the phase change.

In the invention corresponding to claims 3 and 16, in addition to the function corresponding to claims 1 and 14, the measurement means measures the intensity of the elastic wave excited at each of the elastic wave devices, and hence it is possible to obtain the amount of a substance adhered to the surface of the elastic wave device, change in ultrasonic absorption factor of the sensitive film, and gas concentration on the basis of the intensity change.

In the invention corresponding to claims 4 and 17, in addition to the function corresponding to claims 1 and 14, the measurement means simultaneously measures the phase and the intensity of the elastic wave excited at each of the elastic wave devices, and hence it is possible not only to obtain the temperature change from the amount of a substance adhered to the surface of the elastic wave device, elastic change of the sensitive film, gas concentration, and temperature dependence of the elastic wave device based on the phase and intensity, but also to improve the trustworthiness of the measurement by comparing the phase change and intensity change with each other.

In the invention corresponding to claims 5 and 18, in addition to the function corresponding to claims 1 and 14, the measurement means measures the delay time for the reference time of the elastic wave excited at each of the elastic devices, and hence it is possible to obtain the temperature change from the amount of a substance adhered to the surface of the elastic wave device, and temperature dependence of the elastic wave device on the basis of the delay time.

In the invention corresponding to claims 6 and 19, in addition to the function corresponding to claims 1 and 14, input of the high-frequency signal to those elastic wave devices from the first elastic wave device to the last elastic wave device is repetitively executed the averaging times of a number set in advance, further the output signals from each of the elastic wave devices or the measurement data are averaged, and hence it is possible to provide an elastic wave measurement apparatus of high accuracy.

In the invention corresponding to claims 7 and 20, in addition to the function corresponding to claims 1 and 14, when the output signal from the elastic wave device is an analog signal, the detection means detects the output signal after converting the analog signal into a digital signal, and hence it is possible to simultaneously measure the phase and intensity, and also carry out calculation of data, and the like easily.

In the invention corresponding to claims 8 and 21, in addition to the function corresponding to claims 1 and 14, the switching means switches the input destination of the high-frequency signal to each of the elastic wave devices at predetermined time intervals, and hence it is possible to execute efficient switching processing.

In the invention corresponding to claims 9 and 22, in addition to the function corresponding to claims 1 and 14, when the time at which the input destination of the high-frequency signal to the elastic wave devices is switched, and the time at which an output signal from one of the elastic wave devices is detected coincide with each other, the switching means stands by to input the high-frequency signal, and hence it is possible to detect the output signal with a high degree of accuracy.

In the invention corresponding to claims 10 and 23, in addition to the function corresponding to claims 1 and 14, the elastic wave device is a surface acoustic wave device in which the surface acoustic wave is excited on the surface of a piezoelectric substance, and hence it is possible to provide an elastic wave measurement apparatus capable of measuring the response characteristics of the elastic wave at a high speed.

In the invention corresponding to claims 11 and 24, in addition to the function corresponding to claims 10 and 23, in the elastic wave device, the piezoelectric substance is provided with a cylindrical surface, and includes a circling path along which the surface acoustic wave excited on the cylindrical surface circles, and hence it is possible to make the propagation distance of the surface acoustic wave long, and provide a high-accuracy elastic wave measurement apparatus.

In the invention corresponding to claims 12 and 25, in addition to the function corresponding to claims 10 and 23, the elastic wave device is a spherical surface acoustic wave device in which the piezoelectric substance is formed into a spherical shape, and includes a circling path along which the excited surface acoustic wave circles, and hence it is possible to make the propagation distance of the surface acoustic wave long, and provide a high-accuracy elastic wave measurement apparatus.

In the invention corresponding to claims 13 and 26, in addition to the function corresponding to claims 11, 12, 24, and 25, the high-frequency signal is input to each of the elastic wave devices in such a manner that the surface acoustic wave becomes shorter than the circling time in which the surface acoustic wave makes a circuit along the circling path, and hence it is possible obtain output signals separated from each other in terms of time from the elastic wave devices.

While certain embodiments of the inventions have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The various modules of the systems described herein can be implemented as software applications, hardware and/or software modules, or components on one or more computers, such as servers. While the various modules are illustrated separately, they may share some or all of the same underlying logic or code. The accompanying claims and their equivalents are intended to cover such forms or modifications as would fall within the scope and spirit of the inventions.

What is claimed is:

1. An elastic wave measurement apparatus configured to measure response characteristics from a plurality of elastic wave devices, the apparatus comprising:
  a high-frequency signal generator that generates a high-frequency signal that is input to an elastic wave device among the plurality of elastic wave devices based on an input destination;

a switch that sequentially switches the input destination of the high-frequency signal among the plurality of elastic wave devices, from the elastic wave device to which the high-frequency signal is being input to another elastic wave device among the plurality of elastic wave devices, before a detection time at which an output signal from the elastic wave device is detected;

a plurality of detectors each associated with a corresponding elastic wave device among the plurality of elastic wave devices, that each detect an output signal of the corresponding elastic wave device at a time that is
after a detection time of the corresponding elastic wave device,
different for each of the corresponding elastic wave devices, and
based on a predetermined number of circuits for the corresponding elastic wave device;

an analog to digital converter that sequentially receives the detected output signals from the plurality of detectors at the different times; and a measurement device that measures elastic waves excited at each of the elastic wave devices, based on an output from the analog to digital converter.

2. The elastic wave measurement apparatus according to claim 1, wherein the measurement device measures a phase of the elastic wave excited at each of the elastic wave devices.

3. The elastic wave measurement apparatus according to claim 1, wherein the measurement device measures an intensity of the elastic wave excited at each of the elastic wave devices.

4. The elastic wave measurement apparatus according to claim 1, wherein the measurement device simultaneously measures a phase and an intensity of the elastic wave excited at each of the elastic wave devices.

5. The elastic wave measurement apparatus according to claim 1, wherein the measurement device measures a delay time of the elastic wave excited at each of the elastic wave devices for a reference time.

6. The elastic wave measurement apparatus according to claim 1, further comprising:
an averaging unit that averages successive output signals of an elastic wave device to which the high-frequency signal is repetitively input a predetermined number of times.

7. The elastic wave measurement apparatus according to claim 1, wherein when an output signal from an elastic wave device is an analog signal, the associated detector detects the output signal after converting the analog signal into a digital signal.

8. The elastic wave measurement apparatus according to claim 1, wherein the switch switches the input destination of the high-frequency signal from the elastic wave device to the another elastic wave device at predetermined time intervals.

9. The elastic wave measurement apparatus according to claim 1, wherein when a time at which the input destination of the high-frequency signal is switched from the elastic wave device to the another elastic wave device coincides with a time at which the output signal from the another elastic wave devices is detected, the switch stands by to input the high-frequency signal.

10. The elastic wave measurement apparatus according to claim 1, wherein each of the elastic wave devices comprises a surface acoustic wave device in which a surface acoustic wave is excited on a surface of a piezoelectric substance.

11. The elastic wave measurement apparatus according to claim 10, wherein in each of the elastic wave devices, the piezoelectric substance is provided with a cylindrical surface and includes a circular path along which the surface acoustic wave excited on the cylindrical surface loops.

12. The elastic wave measurement apparatus according to claim 10, wherein each of the elastic wave devices comprises a spherical surface acoustic wave device in which a piezoelectric substance is formed into a spherical shape and includes a circular path along which the excited surface acoustic wave loops.

13. The elastic wave measurement apparatus according to claim 11, wherein an input device inputs the high-frequency signal to each of the elastic wave devices in such a manner that the surface acoustic wave becomes shorter than the time in which the surface acoustic wave makes a circuit along the circular path.

14. The elastic wave measurement apparatus according to claim 12, wherein an input device inputs the high-frequency signal to each of the elastic wave devices in such a manner that the surface acoustic wave becomes shorter than the time in which the surface acoustic wave makes a circuit along the circular path.

15. An elastic wave measurement method used for an elastic wave measurement apparatus comprising a plurality of elastic wave devices configured to output response characteristics of elastic waves in accordance with input of a high-frequency signal, a high-frequency signal generator configured to generate the high-frequency signal, and a switch configured to input the high-frequency signal generated by the high-frequency signal generator to each of the elastic wave devices by sequentially switching the input to each of the elastic wave devices, the method comprising:
inputting the high-frequency signal to an elastic wave device among the plurality of elastic wave devices;
switching the high-frequency signal to among the plurality of elastic wave devices, from the elastic wave device the high-frequency signal is being input, to another elastic wave device among the plurality of elastic wave devices, before a detection time at which an output signal from the first elastic wave device is detected;
detecting an output signal of each of the plurality of elastic wave devices at a time that is
after a respective detection time of each of the elastic wave devices,
different for each of the elastic wave devices, and
based on a predetermined number of circuits for each of the elastic wave devices;
providing the detected output signal to an analog to digital converter that sequentially receives the detected output signals;
measuring elastic waves excited at each of the elastic wave devices based on an output from the analog to digital converter.

16. The elastic wave measurement method according to claim 15, wherein detecting the output signal comprises measuring a phase of the elastic wave excited at each of the elastic wave devices.

17. The elastic wave measurement method according to claim 15, wherein measuring the elastic waves comprises measuring an intensity of the elastic wave excited at each of the elastic wave devices.

18. The elastic wave measurement method according to claim 15, wherein measuring the elastic waves comprises simultaneously measuring a phase and an intensity of the elastic wave excited at each of the elastic wave devices.

19. The elastic wave measurement method according to claim 15, wherein in measuring the elastic waves comprises measuring a delay time of the elastic wave excited at each of the elastic wave devices for a reference time.

20. The elastic wave measurement method according to claim 15, further comprising:
averaging successive output signals of an elastic wave device to which the high frequency signal is repetitively input a predetermined number of times.

21. The elastic wave measurement method according to claim 15, wherein when the detected output signal is an analog signal, the output signal is detected after the analog signal is converted into a digital signal.

22. The elastic wave measurement method according to claim 15, wherein the high-frequency signal being input to the elastic wave devices is switched from the elastic wave device to the another elastic wave device at predetermined time intervals.

23. The elastic wave measurement method according to claim 15, wherein when a time at which the high-frequency signal is switched from the elastic wave device to the another elastic wave device coincides with a time at which the output signal from the another elastic wave device is detected, input of the high-frequency signal is made on standby.

24. The elastic wave measurement method according to claim 15, wherein each of the elastic wave devices is a surface acoustic wave device in which a surface acoustic wave is excited on a surface of a piezoelectric substance.

25. The elastic wave measurement method according to claim 24, wherein in each of the elastic wave devices, the piezoelectric substance is provided with a cylindrical surface and includes a circular path along which the surface acoustic wave excited on the cylindrical surface loops.

26. The elastic wave measurement method according to claim 24, wherein each of the elastic wave devices comprises a spherical surface acoustic wave device in which a piezoelectric substance is formed into a spherical shape and includes a circular path along which the excited surface acoustic wave loops.

27. The elastic wave measurement method according to claim 25, wherein the high-frequency signal is input to each of the elastic wave devices in such a manner that the surface acoustic wave becomes shorter than the time in which the surface acoustic wave makes a circuit along the circular path.

28. The elastic wave measurement method according to claim 26, wherein the high-frequency signal is input to each of the elastic wave devices in such a manner that the surface acoustic wave becomes shorter than the time in which the surface acoustic wave makes a circuit along the circular path.

* * * * *

UNITED STATES PATENT AND TRADEMARK OFFICE
CERTIFICATE OF CORRECTION

PATENT NO. : 8,413,516 B2
APPLICATION NO. : 12/659701
DATED : April 9, 2013
INVENTOR(S) : Noguchi et al.

Page 1 of 1

It is certified that error appears in the above-identified patent and that said Letters Patent is hereby corrected as shown below:

In the Specifications:

Column 1, Line 14-17, Below "application." delete "This application is based upon and claims the benefit of priority from prior Japanese Patent Application No. 2007-243073, filed Sep. 19, 2007, the entire contents of which are incorporated herein by reference.".

In the Claims:

Column 20, Line 38, In Claim 15, before "elastic" delete "first".

Signed and Sealed this
Third Day of September, 2013

Teresa Stanek Rea
*Acting Director of the United States Patent and Trademark Office*